United States Patent [19]

Moore et al.

[11] Patent Number: 5,550,268

[45] Date of Patent: Aug. 27, 1996

[54] ION-SENSITIVE COMPOUNDS

[75] Inventors: Christopher P. Moore, Harrow; Trevor J. Wear, South Harrow; Paul D. Beer, North Oxford; Alistair J. Goulden, Bartlemas Close, all of England

[73] Assignee: Eastman Kodak Company, Rochester, N.Y.

[21] Appl. No.: 517,052

[22] Filed: Aug. 21, 1995

[30] Foreign Application Priority Data

Sep. 7, 1994 [GB] England .................... 9418019

[51] Int. Cl.⁶ .................... C07F 17/02
[52] U.S. Cl. .................... 556/145
[58] Field of Search .................... 423/414; 556/138, 556/140, 143, 145

[56] References Cited

PUBLICATIONS

Beer et al., J. Chem. Soc. Chem. Commun. 1993, 229.
Beer et al., J. Organomet. Chem 1989 378 437.

Primary Examiner—Charles T. Jordan
Assistant Examiner—J. R. Hardee
Attorney, Agent, or Firm—John R. Everett

[57] ABSTRACT

An ion sensitive compound has the formula

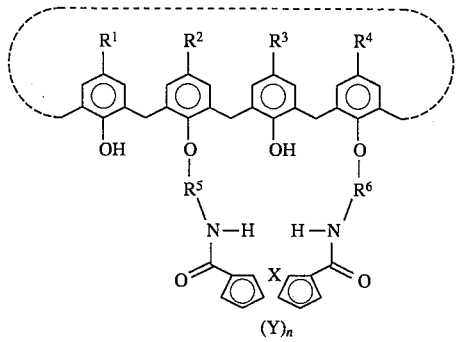

wherein $R^1$, $R^2$, $R^3$ and $R^4$ are each independently hydrogen, a substituted or unsubstituted alkyl group, a substituted or unsubstituted aryl group, an alkylamido group, an arylamido group, an alkylsulfonamido group, an arylsulfonamido group or a nitro group;

$R^5$ and $R^6$ are each independently a substituted or unsubstituted alkylene group;

X is Fe or $Co^+$;

Y is a counter anion; and, n is 0 or 1.

Such compounds can be used for sensing anions.

6 Claims, No Drawings

ION-SENSITIVE COMPOUNDS

FIELD OF THE INVENTION

The invention relates to ion-sensitive compounds. More particularly, the invention relates to ion-sensitive compounds comprising a receptor designed to bind anionic species by the formation of a receptor-substrate complex. The compounds can be used to detect anions in solution by sensing the electrochemical change which results from the formation of the complex.

BACKGROUND OF THE INVENTION

A calix[4] arene ditopic anion receptor molecule containing two cobalticinium moieties capable of coordinating and electrochemically recognising anions has been reported, P. D. Beer, M. G. B. Drew, C. Hazlewood, D. Hesek, J. Hodacova and S. E. Stokes, J. Chem. Soc., Chem. Commun., 1993, 229. Anions recognised include the dicarboxylate anion adipate.

PROBLEM TO BE SOLVED BY THE INVENTION

There is a continuing need to provide new receptor compounds for a variety of applications. For example, there is a need for compounds which can be incorporated in electrochemical sensors for anion determination. There is also a need for compounds which can be used in removal devices where levels of a given anion need to be kept low.

It is also desirable to provide receptor compounds which can be readily synthesised.

SUMMARY OF THE INVENTION

The ion-sensitive compounds of the invention have the formula

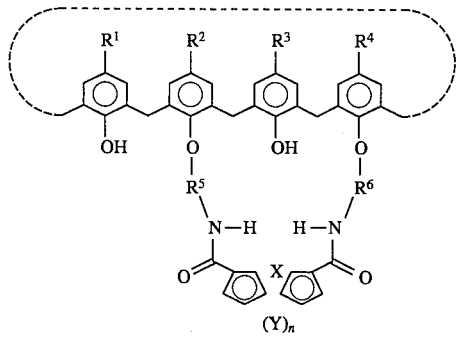

wherein
$R^1$, $R^2$, $R^3$ and $R^4$ are each independently hydrogen, a substituted or unsubstituted alkyl group, a substituted or unsubstituted aryl group, an alkylamido group, an arylamido group, an alkylsulfonamido group, an arylsulfonamido group or a nitro group;
$R^5$ and $R^6$ are each independently a substituted or unsubstituted alkylene group;
X is Fe or $Co^+$;
Y is a counter anion; and,
n is 0 or 1.

The invention also provides a method of sensing an anion in solution by contacting the anion with a receptor for the anion to form a receptor-substrate complex and sensing a detectable change which results from the formation of the complex characterised in that the receptor is a compound of the invention.

ADVANTAGEOUS EFFECT OF THE INVENTION

The compounds of the invention are capable of capturing and electrochemically recognising anions. The compounds can show selectivity for a particular anion in a mixture of anions.

DETAILED DESCRIPTION OF THE INVENTION

Preferably, $R^1$, $R^2$, $R^3$ and $R^4$ are each independently H, a substituted or unsubstituted alkyl group having from 1 to 20 carbon atoms e.g. methyl, ethyl, propyl, butyl, pentyl, hexyl and eicosyl. Tertiary alkyl groups are particularly preferred e.g. t-butyl. Suitable substituents include alkylamido, arylamido, alkoxycarbonyl, aryloxycarbonyl, alkylsulfonamido, arylsulfonamido, alkylcarbonyl, alkoxy, cyano and nitro.

Preferably, $R^1$, $R^2$, $R^3$ and $R^4$ are each independently a substituted or unsubstituted phenyl group. Suitable substituents include alkyloxy, aryloxy, alkylamido, arylamido, alkylsulfonamido, arylsulfonamido, alkyloxycarbonyl, aryloxycarbonyl and nitro.

Preferably, $R^5$ and $R^6$ are each independently an alkylene group having from 1 to 6 carbon atoms e.g. $-(CH_2)_2-$.

Y represents any suitable anion which together with the cobalticinium moiety is capable of forming a stable compound. Examples of such anions include sulphate, nitrate, phosphate, borate and halide e.g. iodide. Preferably, Y represents weakly coordinating anions such as hexafluorophosphate and tetrafluoroborate.

The synthesis of unsubstituted and substituted calixarenes is well documented. By way of example, reference is made to *Calixarenes* by C. David Gutsche, Royal Society of Chemistry, 1989.

Compounds of the invention can be prepared according to the following method. An unsubstituted or substituted calix(4)arene is reacted with two equivalents of haloalkylnitrile to produce the 1,3-biscyano derivative. Subsequent reduction of the cyano groups using, for example, lithium aluminium hydride produces the corresponding 1,3-bisamine derivative. Condensation of the 1,3-bisamine derivative with one equivalent of either 1,1'-bis (chlorocarbonyl) ferrocene or a 1,1'-bis (chlorocarbonyl) cobalticinium salt e.g. chloride, yields a compound of the invention. The counter anion of the cobalticinium salt can be exchanged for a more weakly coordinating anion e.g. hexafluorophosphate, tetrafluoroborate.

The compounds of the invention can be used in a method of sensing anions as indicated above. The detectable change resulting from formation of the complex can be measured by any suitable means such as NMR measurement or electrochemical measurement e.g. cyclic voltammetry.

The invention is further illustrated by way of example as follows.

EXAMPLE 1

5,11,17,23-Tetra-Tert-Butyl-25,27-Bis (Cyanomethoxy)26,28-Dihydroxy-Calix [4]Arene Para-tertiarybutylcalix [4]arene was recrystalised from hot toluene/ethanol and dried under high vacuum.

A slurry of paratertiarybutylcalix [4] arene (3.0 g, 4.05 mmol) and anhydrous potassium carbonate (1.12 g, 8.1 mmol) was stirred in predried acetone (100 ml) at room temperature for 10 mins. Bromoacetonitrile (0.77 ml, 8.1 mmol) was added and the reactants stirred for 48 hours at room temperature. The salt precipitated was removed by filtration and the acetone removed under reduced pressure to leave the crude product. This was taken up in dichloromethane and washed with 1×100 ml $HCl_{(aq)}$ the solvent again removed under reduced pressure to leave the product as a white crystalline solid. Yield 95%.

M.S. (F.A.B) m/z $MH^+$ 727, $MK^+$ 766

I.R. 3500 $cm^{-1}$ broad O-H stretch, 2330 $cm^{-1}$ CN absorption.

$^1H$ N.M.R. ($CDCl_3$,300 MHz) δ:0.69(18H,s,$^tBu$), 1.33(18H,s,$^tBu$), 3.46(4H,d(J=12 Hz), $ArCH_2Ar:H_{eq}$), 4.24(4H,d(J=12 Hz), $ArCH_2Ar:H_{ax}$), 4.62(4H,s, $OCH_2CN$), 5.58(2H,s,O-H), 6.74(4H,s,Ar-H), 7.13(4H,s, Ar-H).

$^{13}C$ N.M.R. ($CDCl_3$,75.42 MHz) δ:30.89($CH_3$), 31.47(C-$CH_3$), 31.53(C-$CH_3$), 31.73($CH_3$), 34.00 ($ArCH_2Ar$), 60.47($CH_2O$), 115.26(CN), 125.51(Ar-C), 126.36(Ar-C), 128.02(Ar-C), 132.03(Ar-C), 142.75(Ar-C), 148.77(Ar-C), 148.93(Ar-C), 150.17(Ar-C)

$^{13}C$ N.M.R.D.E.P.T. ($CDCl_3$,75.42 MHz) δ:30.89($CH_3$), 31.73($CH_3$), 34.00($ArCH_2Ar$), 60.47($CH_2O$), 125.51(ArC-H), 126.36(ArC-H)

5,11,17,23-Tetra-Tert-Butyl-25,27-Bis[Aminoethoxy]-26,28-Dihydroxy-Calix [4]Arene A slurry of the biscyanocalix[4]arene (1.5 g, 2.2 mmol) and lithium aluminium hydride (0.66 g, 17.6 mmol) was refluxed in dry diethylether (75 ml) for 4 hours under a nitrogen atmosphere. The reaction flask was then placed in an ice bath and the excess lithium aluminium hydride destroyed using water (dropwise, vigorous stirring). The alumina precipated was filtered and washed with chloroform and the solvents removed under reduced pressure to leave the product as a white crystalline solid. Yield 75%.

M.S. ($NH_3$D.C.I.) m/z $MH^+$735

I.R. 3600–3300 $cm^{-1}$ broad O-H, N-H stretch.

$^1H$ N.M.R. ($CDCl_3$,300 MHz) δ:1.15(18H,s,$^tBu$), 1.28(18H,s,$^tBu$), 3.35(4H,quin,$CH_2$-$NH_2$) 3.41(4H,d(J= 12 Hz), $ArCH_2Ar:H_{eq}$), 4.08(4H,t,$CH_2$-O), 4.35(4H,d(J= 12 Hz), $ArCH_2Ar:H_{ax}$), 4.77(2H,s,O-H), 7.02(4H,s,Ar-H), 7.08(4H,s,Ar-H), 8.46(4H,br,NH)

5,11,17,23-Tetra-Tert-Butyl-25,27-Bis(1,1'-Bis[Ferrocenecarbomylethoxy])-26,28-Dihydroxy-calixy [4]arene A slurry of 1,3 bisaminecalix[4]arene (0.330 g, 0.45 mmol), dry triethylamine (0.07 ml, 0.495 mmol), a microspatulae of dimethylaminopyridine in dry dichloromethane (75 ml) was stirred under an atmosphere of nitrogen. To this slurry 1,1'-bis (chlorocarbonyl)ferrocene in dry dichloromethane (25 ml) was added dropwise. On completion of the addition the reactants were stirred overnight at room temperature. The solvent was removed under reduced pressure to leave a crude orange solid that was purified using column chromatography. Silica (mesh 230–400); Eluent, Petroleum ether: Ethylacetate (4:1), Rf0.60, Yield 20% of an orange crystalline solid.

M.S. (F.A.B) m/z $MH^+$974

I.R. 1640 $cm^{-1}$ Amide I carbonyl absorption, 1546 $cm^{-1}$ Amide II N-H bend.

$^1H$ N.M.R. ($CDCl_3$,300 MHz) δ:1.02(18H,s,$^tBu$), 1.27(18H,s,$^tBu$), 3.37 (4H,d(J=12 Hz),$ArCH_2Ar:H_{eq}$), 4.06(4H,q,$CH_2NH$), 4.21(4H,t,$CH_2O$), 4.24(4H,d(J=12 Hz), $ArCH_2Ar:H_{ax}$), 4.41(4H,t(J=1.7 Hz),Cp-H), 4.78(4H,t(1.7 Hz),Cp-H), 6.69(4H,s,Ar-H), 7.05(4H,s,Ar-H), 7.62(2H,t(5.4 Hz),$CH_2NH$), 7.63(2H,s,O-H)

$^{13}C$ N.M.R.($CDCl_3$,75.42 Hz) δ:31.00($CH_3$), 31.95($CH_3$) 32.30($ArCH_2Ar$), 34.10(C-$CH_3$), 34.20(C-$CH_3$), 40.07($CH_2$-N), 70.05(Cp-C), 71.90(Cp-C), 76.00($CH_2O$), 78.00(Cp-C), 125.50(Ar-C), 126.00(Ar-C), 128.00(Ar-C), 132.70(Ar-C), 142.50(Ar-C), 147.50(Ar-C), 149.50(Ar-C), 149.90(Ar-C), 171.00(R'COR")

$^{13}C$ N.M.R.D.E.P.T. ($CDCl_3$,75.42 Hz) δ:31.95($CH_3$), 32.30($ArCH_2Ar$), 40.07($CH_2$-N), 70.05(CpC-H), 71.90(CpC-H), 76.00($CH_2O$), 125.50(ArC-H), 126.00(ArC-H)

Example 2

Anion recognition by the compound of Example 1 has been demonstrated by $^1H$ NMR and cyclic voltammetry. Addition of tetrabutyl ammonium halides, hydrogen sulphate and dihydrogen phosphate to solutions of the compound in $Cl_2C_{12}$ solution resulted in perturbations of the receptor's protons. With chloride, the amide proton of the compound of Example 1 is shifted downfield by Δδ 0.3 ppm. Using cyclic voltammetry to compare the redox couple of the free ligand with the anionic complex provides further evidence for anion recognition.

Electrochemical competition experiments with the compound show that when an equimolar mixture of $H_2PO_4^-$, $HSO_4^-$ and $Cl^-$ was added to an acetonitrile electrochemical solution of the compound the ferrocene/ferrocinium redox couple shifted cathodically by an amount approximately the same as that induced by the $H_2PO_4^-$ anion alone. The same result was even obtained when $HSO_4^-$ and $Cl^-$ anions were in tenfold excess concentrations over $H_2PO_4^-$. These results indicate that the receptor would be useful for electrochemically based anion sensors, particularly targeted towards dihydrogen phosphate.

TABLE 1

| Electrochemical data for compound of Example 1[a] | |
|---|---|
| Epa (free, mV)[b] | 450 |
| Epc (free, mV)[b] | 380 |
| ΔE ($H_2PO_4^-$, mV)[c,d] | 110 |
| ΔE ($HSO_4^-$, mV)[c,d] | <5 |
| ΔE ($Cl^-$, mV)[c,d] | 40 |

[a]Obtained in $CH_3CN$ solution containing 0.1M[$NBu_4$] as supporting electrolyte. Solutions were ca. 1 × $10^{-3}$ M in compound and potentials were determined with reference to a $Ag^+$/Ag electrode at 21 ± 1° C., 50 m $Vs^{-1}$ scan rate.
[b]Epa and Epc represent the anodic and cathodic current peak potentials of the ferrocene/ferricinium redox couple of the free ligand.
[c]Cathodic shifts in the ferrocene redox couples produced by presence of anion (5 equiv.) added as their tetrabutylammonium salts.
[d]As the concentration of anion increased the cathodic current peak potential of the ferrocene/ferricinium redox couple began to exhibit the features of an EC mechanism.

We claim:

1. An ion-sensitive compound having the formula

5

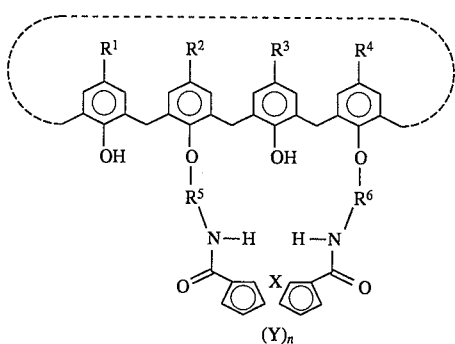

wherein

R¹, R², R³ and R⁴ are each independently hydrogen, a substituted or unsubstituted alkyl group, a substituted or unsubstituted aryl group wherein substituents are selected from alkyloxy, aryloxy, alkylamido, arylamido, alkylsulfonamido, aklyloxycarbonyl, aryloxycarbonyl and nitro; an alkylamido group, an arylamido group, an alkylsulfonamido group, an arylsulfonamido group or a nitro group;

R⁵ and R⁶ are each independently an alkylene group;

X is Fe or Co⁺;

Y is a counter anion; and, n is 0 or 1.

2. A compound according to claim 1 wherein R¹, R², R³ and R⁴ are each independently H, or a substituted or unsubstituted alkyl group having from 1 to 20 carbon atoms.

3. A compound according to claim 1 wherein R¹, R², R³ and R⁴ are each a tertiary alkyl group.

4. A compound according to any one of the preceding claims wherein R⁵ and R⁶ are each independently an alkylene group having from 1 to 6 carbon atoms.

5. A compound according to claim 4 wherein R⁵ and R⁶ are each —(CH₂)ₙ— wherein n is an interger from 1 to 6.

6

6. A method of sensing an anion in solution by contacting the anion with a receptor for the anion to form a receptor-substrate complex and sensing a detectable change which results from the formation of the complex characterised in that the receptor is an ion sensitive compound having the formula

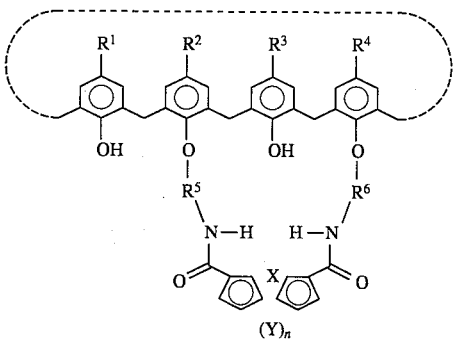

wherein

R¹, R², R³ and R⁴ are each independently hydrogen, a substituted or unsubstituted alkyl group wherein substituents are selected from alkylamido, arylamido, alkoxycarbonyl, aryloxycarbonyl, alklysulfonamido, arylsulfonamido, alkylcarbonyl, alkoxy, cyano and nitro; a substituted or unsubstituted aryl group wherein substituents are selected from alkyloxy, aryloxy, alkylamido, arylamido, alkylsulfonamido, aklyloxycarbonyl, aryloxycarbonyl and nitro; an alkylamido group, an arylamido group, an alkylsulfonamido group, an arylsulfonamido group or a nitro group;

R⁵ and R⁶ are each independently an alkylene group;

X is Fe or Co⁺;

Y is a counter anion; and, n is 0 or 1.

* * * * *